(12) United States Patent
Ghosh et al.

(10) Patent No.: US 7,560,608 B2
(45) Date of Patent: Jul. 14, 2009

(54) METHOD OF PREPARING A XYLENE PRODUCT

(75) Inventors: Ashim Kumar Ghosh, Houston, TX (US); Gopalakrishnan Juttu, Sugar Land, TX (US); Pamela Harvey, Missouri City, TX (US); Neeta Kulkarni, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 113 days.

(21) Appl. No.: 11/876,259

(22) Filed: Oct. 22, 2007

(65) Prior Publication Data

US 2009/0036723 A1 Feb. 5, 2009

Related U.S. Application Data

(62) Division of application No. 10/831,729, filed on Apr. 23, 2004, now Pat. No. 7,285,511.

(51) Int. Cl.
C07C 2/66 (2006.01)
(52) U.S. Cl. .................... 585/466; 585/467
(58) Field of Classification Search ............ 585/466, 585/467
See application file for complete search history.

(56) References Cited

U.S. PATENT DOCUMENTS

| 3,702,886 | A | 11/1972 | Argauer et al. |
|---|---|---|---|
| 3,965,207 | A | 6/1976 | Weinstein |
| 4,115,424 | A | 9/1978 | Unland et al. |
| 4,140,726 | A | 2/1979 | Unland et al. |
| 4,152,364 | A | 5/1979 | Chu |
| 4,250,345 | A | 2/1981 | Chu |
| 4,278,827 | A | 7/1981 | Chu et al. |
| 4,409,132 | A | 10/1983 | Forbus et al. |
| 4,548,914 | A | 10/1985 | Chu |
| 4,554,394 | A | 11/1985 | Forbus et al. |
| 4,590,321 | A | 5/1986 | Chu |
| 4,623,530 | A | 11/1986 | Cullo et al. |
| 4,623,633 | A | 11/1986 | Young |
| 4,638,106 | A | 1/1987 | Pieters et al. |
| 4,665,251 | A | 5/1987 | Chu |
| 4,670,616 | A | 6/1987 | De Simone et al. |
| 4,673,767 | A | 6/1987 | Nimry et al. |
| 4,694,114 | A | 9/1987 | Chu et al. |
| 4,695,666 | A | 9/1987 | Chao et al. |
| 4,695,667 | A | 9/1987 | Sumitani et al. |
| 4,704,495 | A | 11/1987 | Dessau |
| 4,716,135 | A | 12/1987 | Chen |
| 4,721,827 | A | 1/1988 | Cullo et al. |
| 4,727,209 | A | 2/1988 | Chao |
| 4,746,763 | A | 5/1988 | Kocal |
| 4,758,328 | A | 7/1988 | Young |
| 4,761,513 | A | 8/1988 | Steacy |
| 4,847,223 | A | 7/1989 | Le Van Mao et al. |
| 4,861,930 | A | 8/1989 | Cottrell et al. |
| 4,873,067 | A | 10/1989 | Valyocsik et al. |
| 4,891,197 | A | 1/1990 | Derouane et al. |
| 4,891,467 | A | 1/1990 | Sikkenga |
| 4,902,406 | A | 2/1990 | Valyocsik |
| 4,912,073 | A | 3/1990 | Chu |
| 4,914,067 | A | 4/1990 | Pellet et al. |
| 4,935,574 | A | 6/1990 | D'Amore et al. |
| 4,962,255 | A | 10/1990 | Fraenkel et al. |
| 4,973,781 | A | 11/1990 | Valyocsik et al. |
| 5,041,402 | A | 8/1991 | Casci et al. |
| 5,043,502 | A | 8/1991 | Martindale et al. |
| 5,047,141 | A | 9/1991 | Chu |
| 5,068,483 | A | 11/1991 | Barthomeuf et al. |
| 5,094,995 | A | 3/1992 | Butt et al. |
| 5,105,047 | A | 4/1992 | Waller |
| 5,108,579 | A | 4/1992 | Casci |
| 5,110,776 | A | 5/1992 | Chitnis et al. |
| 5,124,299 | A | 6/1992 | Waller |
| 5,171,921 | A | 12/1992 | Gaffney et al. |
| 5,173,461 | A | 12/1992 | Absil et al. |
| 5,178,748 | A | 1/1993 | Casci et al. |
| 5,210,356 | A | 5/1993 | Shamshoum et al. |

(Continued)

FOREIGN PATENT DOCUMENTS

WO WO2005/033071 A2 4/2005

OTHER PUBLICATIONS

Kaeding, W.W., et al., Selective Alkylation of Toluene to Produce para-Xylene, Journal of Catalysis, 1981, pp. 159-174, vol. 67.
Hibino, T., et al., Shape-Selectivity Over HZSM-5 Modified by Chemical Vapor Deposition of Silicon Alkoxide, Journal of Catalysis 128, 1991, pp. 551-558.
Wang, I., et al., Para-selectivity of Diaklybenzenes over Modified HZSM-5 by Vapour Phase Deposition of Silica, Applied Catalysis, 54, 1989, 257-266.
Das, J., et al., Ethylbenzene Dealkylation and Realkylation over Pore Size Regulated MFI Zeolite, Ind. Eng. Chem. Res., 32, 1993, pp. 2525-2529.
Yashima, T., et al., Selective Formation of p-Xylene by Alkylation of Toluene with Methanol on ZSM-5 Type Zeolites, Stud. Surf. Sci. Catal., 1981, 7, pp. 739-751.

(Continued)

*Primary Examiner*—Elizabeth D Wood
(74) *Attorney, Agent, or Firm*—Grady K. Bergen; Jim D. Wheelington; Griggs Bergen LLP (57) ABSTRACT

A method of modifying a zeolite catalyst to increase paraxylene selectivity of the zeolite catalyst in toluene methylation reactions is provided. The method includes forming a slurry of a ZSM-5-type zeolite and an aqueous solution of a phosphorus compound. Water is removed from the slurry to provide a non-steamed, phosphorus treated ZSM-5 zeolite catalyst without deposition of phosphorus onto the catalyst by organophosphorus vapor deposition. The resulting nonsteamed, phosphorus treated ZSM-5 zeolite catalyst has a pore volume of from 0.2 ml/g or less and provides greater than 80% para-xylene selectivity of mixed xylenes when used in toluene methylation.

19 Claims, 5 Drawing Sheets

U.S. PATENT DOCUMENTS

| | | |
|---|---|---|
| 5,227,558 A | 7/1993 | Shamshoum et al. |
| 5,231,064 A | 7/1993 | Absil et al. |
| 5,233,102 A | 8/1993 | Butt et al. |
| 5,246,688 A | 9/1993 | Faust et al. |
| 5,248,841 A | 9/1993 | Young |
| 5,254,767 A | 10/1993 | Dwyer |
| 5,254,770 A | 10/1993 | Olson et al. |
| 5,294,578 A | 3/1994 | Ho et al. |
| 5,315,033 A | 5/1994 | Butt et al. |
| 5,318,696 A | 6/1994 | Kowalski |
| 5,321,183 A | 6/1994 | Chang et al. |
| 5,336,478 A | 8/1994 | Dwyer et al. |
| 5,336,824 A | 8/1994 | Shamshoum et al. |
| 5,345,021 A | 9/1994 | Casci et al. |
| 5,348,643 A | 9/1994 | Absil et al. |
| 5,349,113 A | 9/1994 | Chang et al. |
| 5,365,003 A | 11/1994 | Chang et al. |
| 5,366,948 A | 11/1994 | Absil et al. |
| 5,367,100 A | 11/1994 | Gongwei et al. |
| 5,371,307 A | 12/1994 | Guth et al. |
| 5,378,670 A | 1/1995 | Kumar |
| 5,380,690 A | 1/1995 | Zhicheng et al. |
| 5,385,718 A | 1/1995 | Casci et al. |
| 5,387,732 A | 2/1995 | Shamshoum et al. |
| 5,399,336 A | 3/1995 | Guth et al. |
| 5,430,212 A | 7/1995 | Butt et al. |
| 5,430,213 A | 7/1995 | Hendriksen et al. |
| 5,446,234 A | 8/1995 | Casci et al. |
| 5,455,213 A | 10/1995 | Chang et al. |
| 5,456,821 A | 10/1995 | Absil et al. |
| 5,464,799 A | 11/1995 | Casci et al. |
| 5,475,179 A | 12/1995 | Chang et al. |
| 5,498,814 A | 3/1996 | Chang et al. |
| 5,503,818 A | 4/1996 | Nicolaides |
| 5,516,736 A | 5/1996 | Chang et al. |
| 5,523,510 A | 6/1996 | Pellet et al. |
| 5,534,239 A | 7/1996 | Fajula et al. |
| 5,536,894 A | 7/1996 | Degnan et al. |
| 5,541,146 A | 7/1996 | Chang et al. |
| 5,561,095 A | 10/1996 | Chen et al. |
| 5,563,310 A | 10/1996 | Chang et al. |
| 5,569,805 A | 10/1996 | Beck et al. |
| 5,571,768 A | 11/1996 | Chang et al. |
| 5,573,746 A | 11/1996 | Chen |
| 5,576,256 A | 11/1996 | Monque et al. |
| 5,607,888 A | 3/1997 | Chang et al. |
| 5,607,890 A | 3/1997 | Chen et al. |
| 5,646,314 A | 7/1997 | Crocco et al. |
| 5,648,580 A | 7/1997 | Chen et al. |
| 5,658,454 A | 8/1997 | Absil et al. |
| 5,675,047 A | 10/1997 | Beck et al. |
| 5,689,024 A | 11/1997 | Schmitt |
| 5,698,756 A | 12/1997 | Beck et al. |
| 5,780,563 A | 7/1998 | Chen et al. |
| 5,789,335 A | 8/1998 | Chen et al. |
| 5,811,613 A | 9/1998 | Bhat et al. |
| 5,833,840 A | 11/1998 | Absil et al. |
| 5,847,255 A | 12/1998 | Ghosh et al. |
| 5,902,919 A | 5/1999 | Chen et al. |
| 5,905,051 A | 5/1999 | Wu et al. |
| 5,907,073 A | 5/1999 | Ghosh |
| 5,922,922 A | 7/1999 | Harris et al. |
| 5,925,586 A | 7/1999 | Sun |
| 5,939,597 A | 8/1999 | Dessau et al. |
| 5,951,963 A | 9/1999 | He et al. |
| 5,955,641 A | 9/1999 | Chen et al. |
| 5,990,031 A | 11/1999 | Ghosh |
| 5,994,603 A | 11/1999 | Mohr et al. |
| 6,034,283 A | 3/2000 | Ban et al. |
| 6,040,257 A | 3/2000 | Drake et al. |
| 6,046,128 A | 4/2000 | Kisen et al. |
| 6,047,544 A | 4/2000 | Yamamoto et al. |
| 6,048,816 A | 4/2000 | Brown et al. |
| 6,057,485 A | 5/2000 | Merrill et al. |
| 6,060,633 A | 5/2000 | Chen et al. |
| 6,074,975 A | 6/2000 | Yao et al. |
| 6,080,303 A | 6/2000 | Cao et al. |
| 6,080,698 A | 6/2000 | Zhang et al. |
| 6,083,865 A | 7/2000 | Drake et al. |
| 6,090,274 A | 7/2000 | Wu et al. |
| 6,090,991 A | 7/2000 | Butler et al. |
| 6,096,938 A | 8/2000 | Ghosh |
| 6,100,437 A | 8/2000 | Koehl et al. |
| 6,124,227 A | 9/2000 | Yao et al. |
| 6,150,293 A | 11/2000 | Verduijn et al. |
| 6,156,949 A | 12/2000 | Brown et al. |
| 6,160,191 A | 12/2000 | Smith et al. |
| 6,187,982 B1 | 2/2001 | Beck et al. |
| 6,211,104 B1 | 4/2001 | Shi et al. |
| 6,217,748 B1 | 4/2001 | Hatanaka et al. |
| 6,222,084 B1 | 4/2001 | Ghosh et al. |
| 6,251,263 B1 | 6/2001 | Hatanaka et al. |
| 6,268,305 B1 | 7/2001 | Butler et al. |
| 6,294,493 B1 | 9/2001 | Strohmaier et al. |
| 6,300,535 B1 | 10/2001 | van den Berge et al. |
| 6,306,790 B1 | 10/2001 | Rodriguez et al. |
| 6,342,153 B1 | 1/2002 | Guan et al. |
| 6,388,156 B1 | 5/2002 | Ou et al. |
| 6,395,664 B1 | 5/2002 | Boehner et al. |
| 6,399,530 B1 | 6/2002 | Chen et al. |
| 6,417,421 B1 | 7/2002 | Yao |
| 6,423,879 B1 | 7/2002 | Brown et al. |
| 6,444,610 B1 | 9/2002 | Yamamoto |
| 6,459,006 B1 | 10/2002 | Ou et al. |
| 6,469,095 B1 | 10/2002 | Gareiss et al. |
| 6,503,862 B1 | 1/2003 | Yamamoto |
| 6,504,072 B1 | 1/2003 | Brown et al. |
| 6,504,074 B2 | 1/2003 | Verduijn et al. |
| 6,506,954 B1 | 1/2003 | Brown et al. |
| 6,518,213 B1 | 2/2003 | Yamamoto et al. |
| 6,548,725 B2 | 4/2003 | Froment et al. |
| 6,566,293 B1 | 5/2003 | Vogt et al. |
| 6,589,901 B2 | 7/2003 | Yamamoto et al. |
| 6,613,708 B1 | 9/2003 | Ou et al. |
| 6,613,951 B1 | 9/2003 | Brown et al. |
| 6,642,426 B1 | 11/2003 | Johnson et al. |
| 6,689,929 B2 | 2/2004 | Williams et al. |
| 6,699,811 B1 | 3/2004 | Mohr et al. |
| 6,723,297 B2 | 4/2004 | Chen et al. |
| 6,726,834 B2 | 4/2004 | Quesada et al. |
| 6,770,251 B2 | 8/2004 | Yoshikawa |
| 6,773,694 B1 | 8/2004 | Lesch et al. |
| 6,799,089 B2 | 9/2004 | Toulhoat |
| 6,811,684 B2 | 11/2004 | Mohr et al. |
| 6,812,181 B2 | 11/2004 | van der Berge et al. |
| 2003/0004383 A1 | 1/2003 | Brown et al. |

OTHER PUBLICATIONS

Sayed, M. B., et al., The Effect of Modification with Boron on the Catalytic Activity and Selectivity of HZSM-5, Journal of Catalysis 101, 1986, pp. 43-55.

Kim, J.-H., et al., Para-selectivity of Metallosilicates with MFI Zeolite Structure Zeolites, vol. 11, 1991, pp. 59-63.

Kim, J.-H., et al., Preparation of Highly Para-selective Metallosilicate Catalysts for Alkylation of Ethylbenzene with Ethanol, Applied Catalysis A:100, 1993, pp. 27-36.

Kim, J.-H, et al., Generation of Shape-Selectivity of p-Xylene Formation in the Synthesized ZSM-5 Zeolites, Journal of Catalysis 173, 1998, pp. 433-439.

Sayed, M. B., et al., The Effect of Boron on ZSM-5 Zeolite Shape Selectivity and Activity, Journal of Catalysis 116, 1989, pp. 1-10.

METHOD OF PREPARING A XYLENE PRODUCT

This application is a division of U.S. patent application Ser. No. 10/831,729, entitled "Method of Modifying Zeolite Catalyst," filed Apr. 23, 2004, now U.S. Pat. No. 7,285,511, which is herein incorporated by reference in its entirety.

TECHNICAL FIELD

The invention relates generally to the alkylation of aromatic compounds and catalysts used for such reactions.

BACKGROUND

Para-xylene is a valuable substituted aromatic compound due to its great demand for production of terephthalic acid, a major component in forming polyester fibers and resins. It can be commercially produced from hydrotreating of naphtha (catalytic reforming), steam cracking of naphtha or gas oil, and toluene disproportionation.

Alkylation of toluene with methanol, which is also known as toluene methylation, has been used in laboratory studies to produce para-xylene. Toluene methylation has been known to occur over acidic catalyst, particularly over zeolite or zeolite-type catalyst. In particular, ZSM-5-type zeolite, zeolite Beta and silicaaluminophosphate (SAPO) catalysts have been used for this process. Generally, a thermodynamic equilibrium mixture of ortho (o)-, meta (m)- and para (p)-xylenes can be formed from the methylation of toluene, as is illustrated by the reaction below.

Thermodynamic equilibrium compositions of o-, m-, and p-xylenes may be around 25, 50 and 25 mole %, respectively, at a reaction temperature of about 500° C. Such toluene methylation may occur over a wide range of temperatures, however. Para-xylene can be separated from mixed xylenes by a cycle of adsorption and isomerization. Byproducts such as C9+ and other aromatic products can be produced by secondary alkylation of the xylene product.

A significantly higher amount of p-xylene can be obtained in toluene methylation reaction if the catalyst has shape selective properties. Shape selective properties can be obtained in modified zeolite catalysts by modifying zeolite pore opening size, inactivation of the external surface of the zeolite or controlling zeolite acidity. Toluene methylation may occur over modified ZSM-5 or ZSM-5-type zeolite catalyst giving xylene products containing significantly greater amounts of p-xylene than the thermodynamic concentration.

Phosphoric acid and other phosphorus-containing compounds have been used to modify ZSM-5 zeolite catalysts to provide shape selective properties. U.S. Pat. No. 6,504,072, for instance, discloses the treatment of ZSM-5 zeolite catalyst with phosphorus to control the reduction of diffusivity and pore volume prior to severe steaming to provide a para-selective catalyst. U.S. Pat. No. 4,554,394 discusses the treatment of ZSM-5 zeolites with a vapor phase organophosphorus reagent to provide para-selective properties.

Unfortunately, there are a number of technical hurdles for toluene methylation to be commercially successful and improvements are needed.

BRIEF DESCRIPTION OF THE DRAWINGS

For a more complete understanding of the present invention, reference is now made to the following descriptions taken in conjunction with the accompanying figures, in which.

DETAILED DESCRIPTION

As used herein, the expression "ZSM-5-type" is meant to refer to those zeolites that are isostructurally the same as ZSM-5 zeolites. Additionally, the expressions "ZSM-5" and "ZSM-5-type" may be used herein interchangeably to encompass one another and should not be construed in any limiting sense. The ZSM-5 zeolite catalysts and their preparation are described in U.S. Pat. No. 3,702,886, which is herein incorporated by reference.

As used herein, catalytic activity can be defined as the production of total xylenes as measured by the weight % of total xylenes in the liquid product stream obtained at a given toluene methylation reaction conditions. As used herein, the total xylenes selectivity can be defined as:

$$\% \text{ Total Xylenes Selectivity} = (X_{tx}/X_{tap}) \times 100 \tag{2}$$

where, $X_{tx}$ is the weight % of total xylenes and $X_{tap}$ is the weight % of total aromatic products in the liquid product stream. As used herein, selectivity for p-xylene may be expressed as:

$$\% \text{ p-Xylene Selectivity} = (X_p/X_{tx}) \times 100 \tag{3}$$

where, $X_p$ is the weight % p-xylene in the liquid product stream.

By modifying ZSM-5 zeolite catalysts with phosphorus containing compound to provide a selected pore volume, increased para-selectivity may be achieved without the need for subsequent steaming or additional treatment of the catalyst. Furthermore, increased catalyst activity and total xylenes selectivity may be achieved during use in toluene methylation for particular ZSM-5 zeolite catalysts, while still providing high p-xylene selectivity.

The starting ZSM-5 zeolite may be an $NH_4$- or H-form zeolite, which may be in the form of a powder or any other form. In the present invention, the ZSM-5 zeolite catalyst may include those having a silica/alumina molar ratio of greater than 25 prior to modification with a phosphorus-containing compound. As is discussed below, the silica/alumina ratio of the initial ZSM-5 zeolite catalyst may have an effect on catalyst activity and xylene selectivity of the subsequently treated catalyst in toluene methylation. In certain instances, the $SiO_2/Al_2O_3$ mole ratio of starting ZSM-5 may be from 250, 280, 300 to 1000 or more to achieve higher activity with increased p-xylene selectivity.

The phosphorus compound may be a phosphorus-containing acid, such as phosphoric acid ($H_3PO_4$) and phosphorus acid ($H_3PO_3$). For phosphorus-containing acids, the acid may be used at a concentration of greater than 50 wt %. The phosphorus compound may also include other non-acid phosphorus-containing compounds, such as ammonium hydrogen phosphate (($NH_4$)$_2HPO_4$). The amount of phosphorus used may provide a phosphorus content of the treated catalyst of from 0.04 g P/g zeolite or more. In certain applications, phosphorus may be incorporated into the catalyst in amounts of from 0.09 g P/g zeolite or more, with from about 0.09 g P/g zeolite to about 0.15 g P/g zeolite being suitable in such applications.

The phosphorus may be incorporated into the catalyst by preparing a slurry of the zeolite and an aqueous solution of the phosphorus compound. Heating of the slurry may be used to facilitate treatment of the zeolite catalyst and to evaporate liquids. Heating of the slurry to temperatures of from 70° C. to about 100° C. is suitable in most instances. The slurry may also be stirred or agitated during this step to ensure uniform treatment.

The phosphorus-modified zeolite catalyst may be used unbound or be bound with a binder. Examples of suitable binders include such materials as alumina, clay, and silica. Those techniques used for preparing the bound catalyst are well known in the art. The catalyst, bound or unbound, may be calcined at a temperature between 400° C. and 570° C. in an environment containing oxygen, typically air.

The treated ZSM-5 zeolite catalyst should provide a total pore volume of from about 0.2 ml/g or less. More particularly, the total pore volume may range from about 0.18 ml/g to about 0.07 ml/g. The BET surface area of the ZSM-5 zeolite catalyst may range from less than 300 m²/g to about 10 m²/g.

The phosphorus-modified catalyst contains an insignificant amount of tetrahedral/structural Al in the zeolite framework showing a weak $^{27}$Al-NMR peak at around 50 ppm, but the catalyst contains "debris" or extra framework aluminum (EFAl) inside zeolite pores showing a strong $^{27}$Al-NMR peak at −14 ppm. The ratio of framework aluminum over extra-framework aluminum for the treated zeolite catalyst may range from about 0.12 to 0.25.

The treated catalyst may be used as a non-steamed catalyst in toluene methylation. As used herein, "non-steamed," as it refers to the zeolite catalyst, is meant to include zeolite catalyst that has not been treated or subjected to high temperature steam (i.e. greater than 950° C.) to effect structural changes of the catalyst prior to its use in any alkylation or methylation reactions.

The modified catalyst may be contacted with an appropriate feed of toluene and methanol under methylation reaction conditions to carry out toluene methylation. A hydrogen cofeed may also be used. The hydrogen may be used in an amount of at least 0.1 mole per mole of toluene/methanol feed.

Water or steam may also be introduced into the reactor as cofeed along with the toluene/methanol feed. The water or steam used for the methylation reaction may be introduced with or without hydrogen as cofeed with the hydrocarbon feed to the reactor during the start up of the methylation reaction or it may be introduced subsequent to initial start up. In either case, liquid water may be added and vaporized prior to its mixing with hydrogen cofeed (if any) and hydrocarbon feed.

The reactor pressure for toluene methylation or other aromatic alkylation may vary, but typically ranges from about 10 to about 1000 psig. Reactor temperatures may range from 400 to 700° C.

The reaction may be carried in a variety of different reactors that are commonly used for carrying out aromatic alkylation reactions. Single or multi reactors in series and/or parallel are suitable for carrying out the toluene methylation.

The modified catalyst is useful in toluene methylation for preparing a xylene product from a feed of toluene and methanol that has increased selectivity for p-xylene. In particular, the catalyst may provide greater than 80%, 85% and 90% para-xylene selectivity when used in toluene methylation. Additionally, in certain instances, greater than 90% of total xylene selectivity may be achieved.

The following examples further illustrate the invention.

EXAMPLES

Catalyst Preparation

Catalyst A-H

The starting material was an $NH_4$-ZSM-5 zeolite powder having a $SiO_2/Al_2O_3$ mole ratio of 30. An aqueous slurry containing 11.63 g of $NH_4$-ZSM-5 zeolite and 50 ml of deionized water was prepared in a 400 ml beaker. The beaker was placed on a hot plate and the zeolite suspension was stirred using a magnetic stir bar. The temperature of the suspension was maintained around 90° C. 1.08 g phosphoric acid (85 wt % in aqueous) was added drop wise into the beaker. Heating was continued until all liquid was evaporated. The phosphoric-acid modified zeolite was dried at 90° C. to 120° C. for at least four hours and at 340° C. to 360° C. for three hours and then calcined at 510° C. to 530° C. under air for 10 hours. The calcined zeolite was then crushed and sized using 20 and 40 mesh screens. A series of catalysts A-H (see Table 1) were prepared by varying the amount of phosphoric acid with respect to the amount of starting $NH_4$-ZSM-5 powder. BET surface area and total pore volume (measured by $N_2$ adsorption) for catalysts A-H are shown in Table 1 and in FIGS. 1 and 2.

TABLE 1

| Catalyst | Water, ml | Zeolite Powder, g | $H_3PO_4$ Content, g[a] | P, g/g zeolite[a] | SA, m2/g | PV, ml/g |
|---|---|---|---|---|---|---|
| A | 100 | 46.50 | 4.00 | 0.023 | 266.4 | 0.483 |
| B | 50 | 11.63 | 1.08 | 0.025 | 259.0 | 0.340 |
| C | 50 | 11.63 | 2.52 | 0.058 | 157.8 | 0.212 |
| D | 50 | 11.64 | 4.04 | 0.093 | 66.9 | 0.189 |
| E | 50 | 11.63 | 6.01 | 0.139 | 24.0 | 0.183 |
| F | 50 | 11.63 | 8.05 | 0.186 | 18.6 | 0.179 |

TABLE 1-continued

| Catalyst | Water, ml | Zeolite Powder, g | H$_3$PO$_4$ Content, g[a] | P, g/g zeolite[a] | SA, m2/g | PV, ml/g |
|---|---|---|---|---|---|---|
| G | 50 | 11.64 | 12.51 | 0.279 | 14.2 | 0.077 |
| H | 50 | 11.64 | 16.01 | 0.370 | 9.7 | 0.079 |
| I | | | 0 | 0 | 357.2 | 0.579 |

Figure 1:
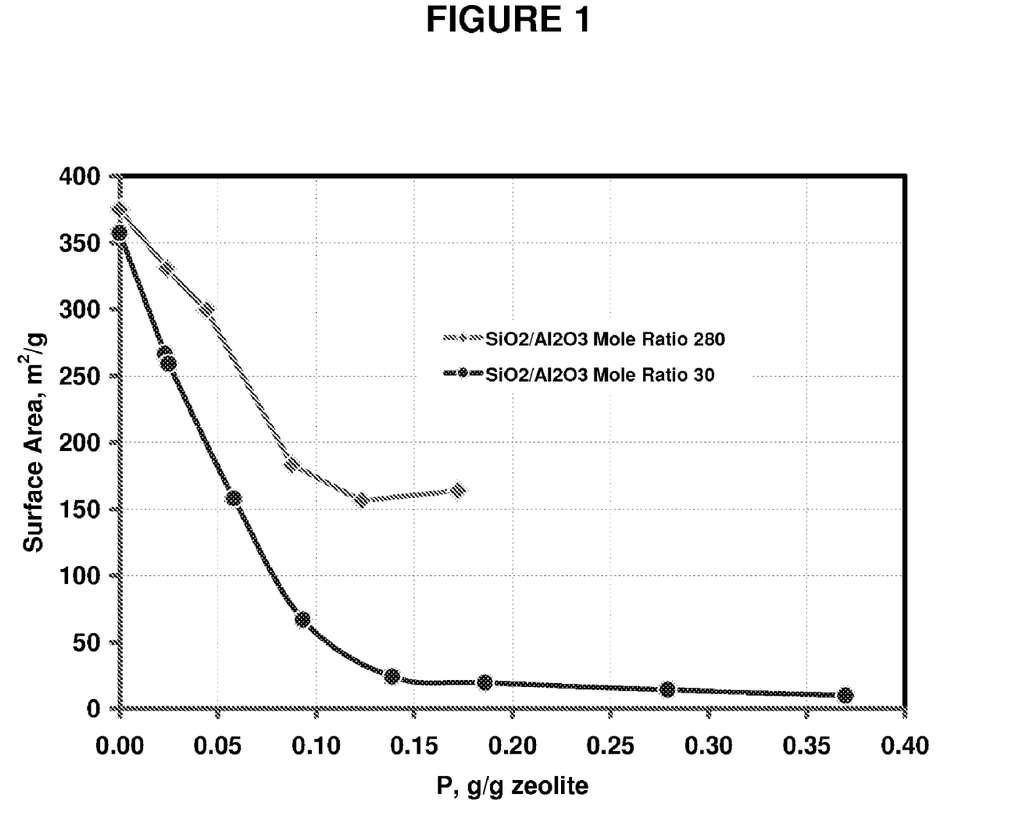
FIG. 1 is a plot of BET surface area of different $H_3PO_4$ modified ZSM-5 zeolite catalysts as a function of the amount of phosphorus used in the modification.
Figure 2:
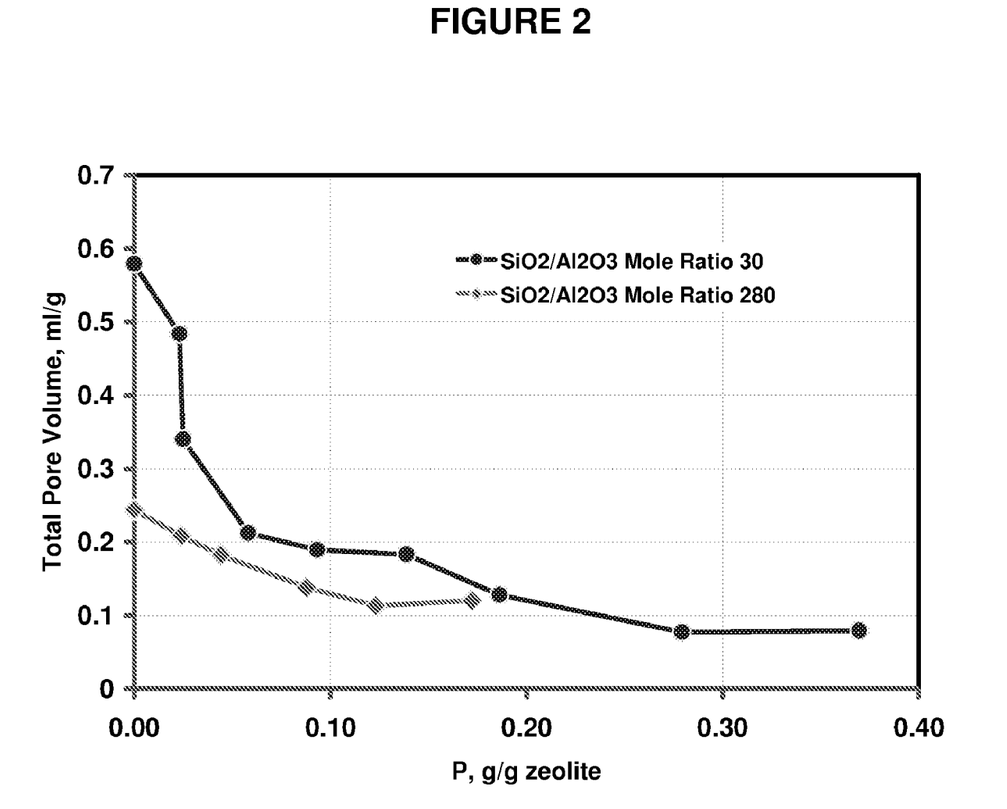
FIG. 2 is a plot of total pore volume of different $H_3PO_4$ modified ZSM-5 zeolite catalysts as a function of the amount of phosphorus used in the modification.

[a]Total amount of phosphoric acid (85% in aqueous) or P used in the preparation As can be seen from Table 1 and FIGS. 1 and 2, a sharp decrease in BET surface area (SA) and total pore volume (PV) of the zeolite catalysts A-H prepared by using starting NH$_4$-ZSM-5 having SiO$_2$/Al$_2$O$_3$ mole ratio of 30 with increasing amounts of phosphoric acid or P was observed.

Catalyst J-N

The starting material was an NH$_4$-ZSM-5 zeolite powder having a SiO$_2$/Al$_2$O$_3$ mole ratio of 280. A slurry containing 12.09 g of NH$_4$-ZSM-5 zeolite and 50 ml of deionized water was prepared in a 400 ml beaker. The beaker was placed on a hot plate and the zeolite suspension was stirred using a magnetic stir bar. The temperature of the suspension was maintained around 90° C. 1.08 g phosphoric acid (85 wt % in aqueous) was added drop wise into the beaker. Heating was continued until all liquid was evaporated. The phosphoric-acid modified zeolite was dried at 90° C. to 120° C. for at least four hours and at 340° C. to 360° C. for three hours and then calcined at 510° C. to 530° C. under air for 10 hours. The calcined zeolite was then crushed and sized using 20 and 40 mesh screens. A series of catalysts J-N (see Table 2) were prepared by varying the amount of phosphoric acid with respect to the amount of starting NH$_4$-ZSM-5 powder. BET surface area and total pore volume (measured by N$_2$ adsorption) for catalysts J-N are shown in Table 2 and FIGS. 1 and 2. The decrease in SA and PV for catalyst made using starting NH$_4$-ZSM-5 having SiO$_2$/Al$_2$O$_3$ mole ratio 280 is not as prominent compared to that for catalysts A-J prepared by using starting NH$_4$-ZSM-5 having SiO$_2$/Al$_2$O$_3$ mole ratio 30.

TABLE 2

| Catalyst | Water, ml | Zeolite Powder, g | H$_3$PO$_4$ Content, g[a] | P, g/g zeolite[a] | SA, m2/g | PV, ml/g |
|---|---|---|---|---|---|---|
| J | 50 | 12.09 | 1.08 | 0.024 | 330.7 | 0.208 |
| K | 50 | 24.09 | 3.95 | 0.044 | 299.4 | 0.182 |
| L | 100 | 48.38 | 15.8 | 0.088 | 183.2 | 0.138 |
| M | 100 | 48.39 | 23.7 | 0.123 | 156.2 | 0.113 |
| N | 50 | 12.09 | 7.75 | 0.172 | 163.7 | 0.120 |
| O | | | 0 | 0 | 375.0 | 0.244 |

[a]Total amount of phosphoric acid (85% in aqueous) or P used in the preparation.

Catalyst P-S

The starting material was an NH$_4$-ZSM-5 zeolite powder having a SiO$_2$/Al$_2$O$_3$ mole ratio of 280. A slurry containing 51.66 g of NH$_4$-ZSM-5 zeolite and 200 ml of deionized water was prepared in a 400 ml beaker. The beaker was placed on a hot plate and the zeolite suspension was stirred using a magnetic stir bar. The temperature of the suspension was maintained around 90° C. 9.07 g ammonium hydrogen phosphate, (NH$_4$)$_2$HPO$_4$, was dissolved in 50 ml water and the salt solution was added drop wise into the beaker. Heating was continued until all liquid was evaporated. The ammonium hydrogen phosphate modified zeolite was dried at 90° C. to 120° C. for at least four hours and at 340° C. to 360° C. for three hours and then calcined at 510° C. to 530° C. under air for 10 hours. The calcined zeolite was then crushed and sized using 20 and 40 mesh screens. A series of catalysts P-S (see Table 3) were prepared by varying the amount of ammonium hydrogen phosphate with respect to the amount of starting NH$_4$-ZSM-5 powder. BET surface area and total pore volume (measured by N$_2$ adsorption) for catalysts P-S are shown in Table 3.

TABLE 3

| Catalyst# | Water, ml | Zeolite Powder, g | (NH4)2HPO$_4$, g[a] | P, g/g zeolite[a] | SA, m2/g | PV, ml/g |
|---|---|---|---|---|---|---|
| P | 200 | 30.09 | 2.49 | 0.018 | 317.2 | 0.208 |
| Q | 200 | 51.66 | 9.07 | 0.039 | 278.3 | 0.179 |
| R | 200 | 51.66 | 12.85 | 0.055 | 241.0 | 0.155 |
| S | 200 | 48.38 | 18.14 | 0.082 | 216.2 | 0.131 |

[a]Total amount of ammonium hydrogen phosphate or P used in the preparation

There was little or no difference in surface area and pore volume between the catalyst series J-N using phosphoric acid and P-S using ammonium hydrogen phosphate at a given amount of phosphorus. Thus the use of phosphoric acid or ammonium hydrogen phosphate as a phosphorus-containing compound for preparing p-xylene selective catalysts may not make a significant difference.

Comparative Catalysts I & O

Non-phosphorus containing ZSM-5 zeolite catalysts were prepared for comparison purposes. The starting material was either an NH$_4$-ZSM-5 zeolite powder having a SiO$_2$/Al$_2$O$_3$ mole ratio of 30 or an NH$_4$-ZSM-5 zeolite powder having a SiO$_2$/Al$_2$O$_3$ mole ratio of 280. The zeolite powder was dried at 340° C. to 360° C. for three hours and then calcined at 510° C. to 530° C. under air for 10 hours. The calcined sample was then pressed and sized using 20 and 40 mesh screens for use in a reactor for toluene methylation reaction. Properties for catalysts I and O are presented in Tables 1 and 2, respectively.

$^{27}$Al MAS-NMR

Magic angle spinning (MAS) solid state NMR studies were performed on the starting NH$_4$-ZSM-5 zeolite having SiO$_2$/Al$_2$O$_3$ mole ratio 280 and the phosphorus modified catalyst samples. Measurements used 400 MHz spectrometer ($^{27}$Al at 104.5 MHz), room temperature, silicon nitride rotors (Si$_3$N$_4$), 13 to 14 KHz sample spinning (about 800000 rpm), 10 degree tip to avoid saturation and 4000-10000 scans signal averaging. Proton decoupling was not employed. All spectra were referenced to aluminum chloride hexahydrate (run separately in a tube) at 0.0 ppm on the chemical shift scale. This leads to an internal reference of 104.85 ppm on the aluminum nitride (small impurity in the silicon nitride rotors).

Figure 3:
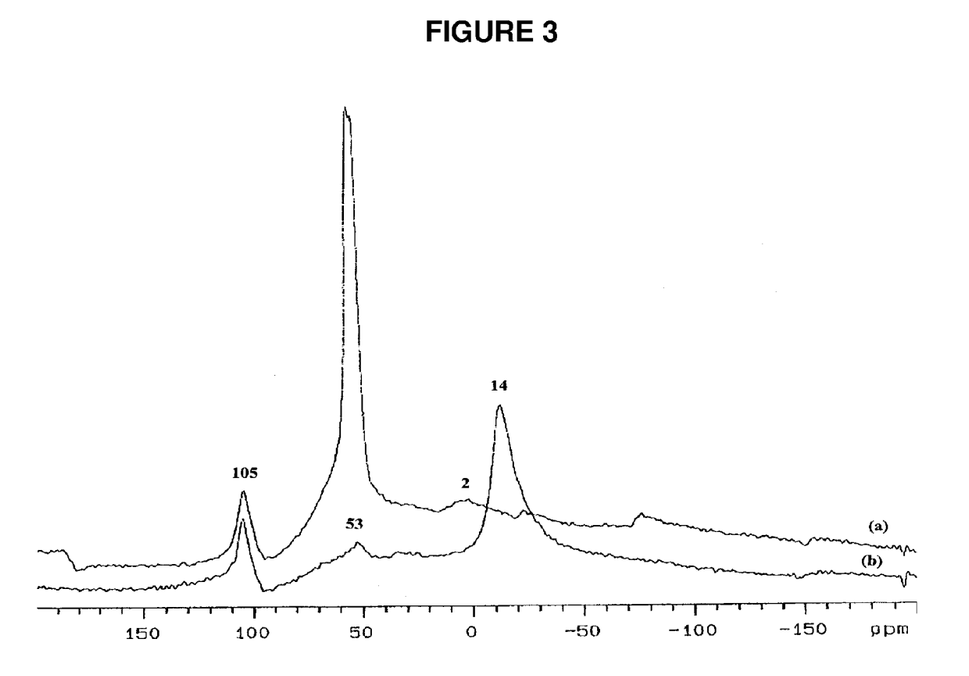
FIG. 3 shows $^{27}$Al MAS-NMR spectra of (a) $NH_4$-ZSM-5 having $SiO_2/Al_2O_3$ mole ratio 280, and of (b) phosphorus modified ZSM-5 zeolite catalyst.

The starting NH$_4$-ZSM-5 zeolite sample showed a strong $^{27}$Al MAS-NMR peak at around 55 ppm attributing to framework tetrahedral (4 coordinated) aluminum (spectrum a, FIG. 3). The sharpness of the resonance and the symmetry indicate the zeolite is relatively crystalline with very few lattice defects. The framework Al is responsible for zeolite acidity and the starting zeolite sample showed strong acidity. The P-modified sample shows a weak peak at 55-50 ppm region assigned to structural tetrahedral aluminum (spectrum b, FIG. 3). The tetrahedral aluminum peak is severely distorted indicating presence of nested silanols caused by holes in the structure upon removal of some of the framework aluminum. The adjacent peak (30-40 ppm) peak is due to severely distorted but still in the framework aluminum atoms probably either in the 3 or 5 coordination with oxygens. The biggest peak in the spectrum at −14 ppm is from octahedrally coordinated aluminum atoms that are formed when tetrahedrally coordinated framework aluminum is removed from the zeolite framework by the phosphate modification process as mentioned above.

Examples 1-19

Figure 4:
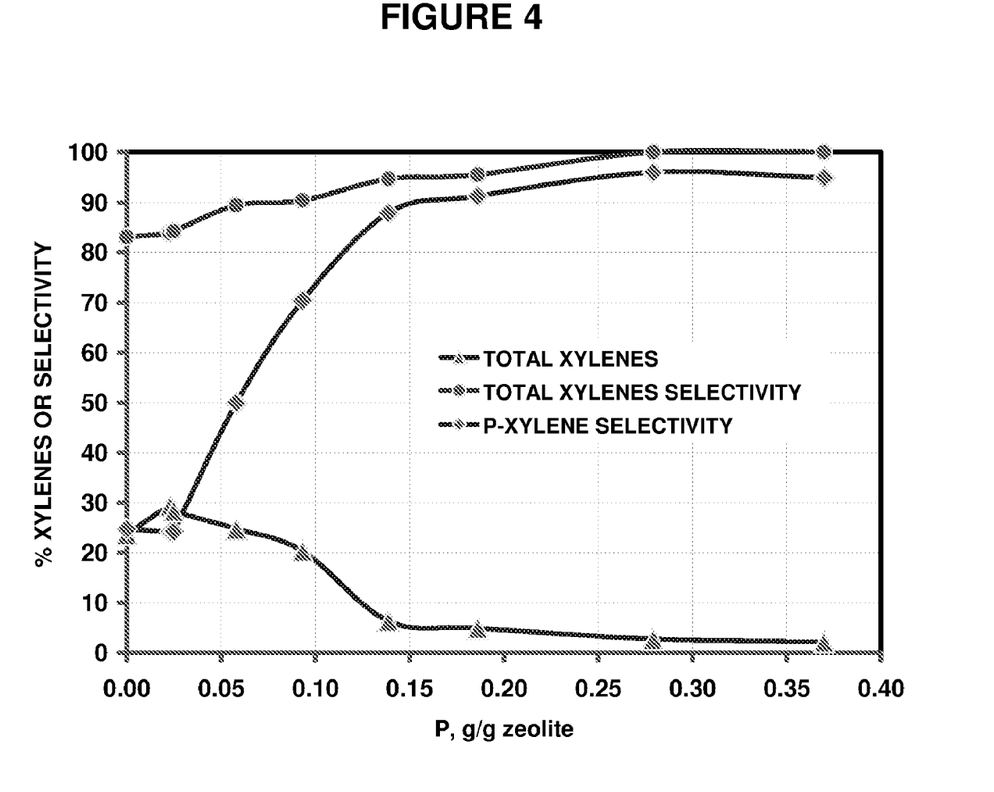
FIG. 4 is a plot of wt % total xylenes and selectivity to total xylenes and p-xylene for a liquid product stream obtained from toluene methylation over $H_3PO_4$ modified ZSM-5 zeolite catalysts having a starting $SiO_2/Al_2O_3$ mole ratio of 30 as a function of amount of phosphorus used in the modification.
Figure 5:
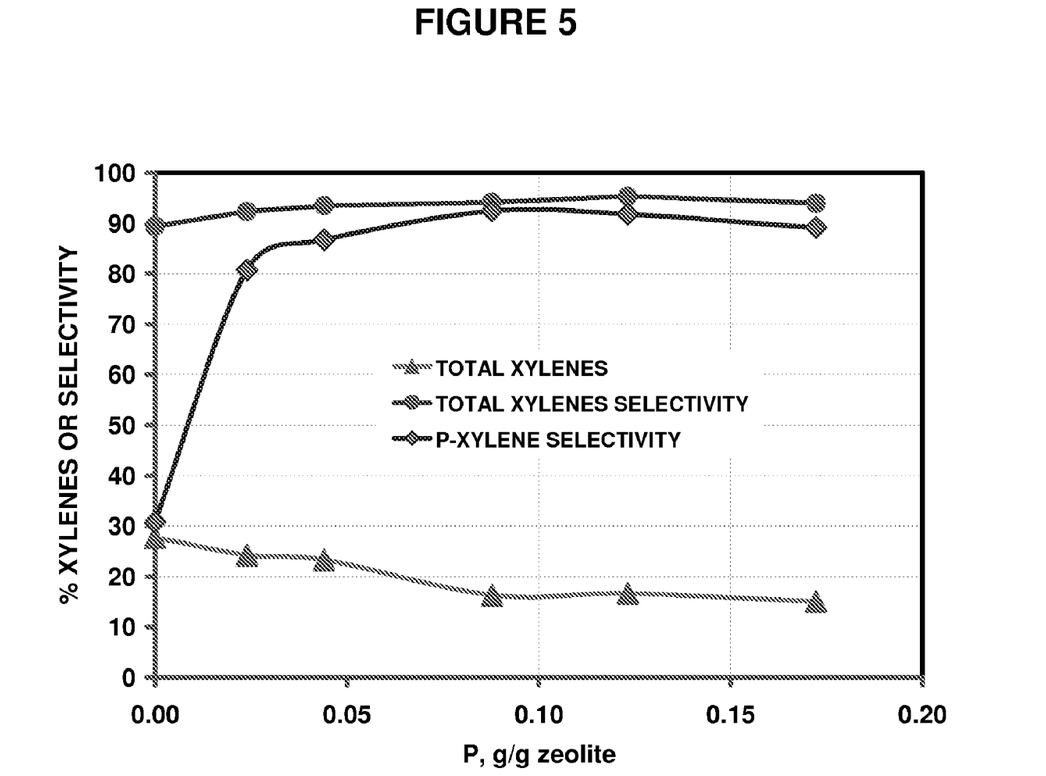
FIG. 5 is a plot of wt % total xylenes and selectivity to total xylenes and p-xylene for a liquid product stream obtained from toluene methylation over $H_3PO_4$ modified ZSM-5 zeolite catalysts having a starting $SiO_2/Al_2O_3$ mole ratio of 280 as a function of amount of phosphorus used in the modification.

The catalysts A-I, J-O and P-S described above and in Tables 1-3, were used in toluene methylation reactions. The reactions were each carried out in a fixed bed, continuous flow type reactor. In each case, a catalyst was dried by slowly raising the catalyst bed temperature (about 5° C./min) to 200° C. under hydrogen ($H_2$) flow for at least one hour. A premixed toluene and methanol feed (molar ratio 2/1) was added to the reactor at 200° C. and the catalyst bed inlet temperature was increased to about 500° C. The liquid hourly space velocity (LHSV) (based on toluene/methanol feed) was maintained at about 31 $hr^{-1}$ and a cofeed of $H_2$ gas was fed and maintained to provide a $H_2$/HC molar ratio of about 0.1. Water was added to the hydrocarbon (HC) feed and was vaporized prior to introduction to reactor. The $H_2O$/HC molar ratio was about 0.65 and reactor pressure was about 20 psig. Liquid products were collected at about 3-4 hours of run time and were analyzed. The following results, as presented in Tables 4-6. FIG. 4 is a plot of para-xylene selectivity and selectivity for total xylenes for catalysts A-I. FIG. 5 is a plot of para-xylene selectivity and selectivity for total xylenes for catalysts J-O.

TABLE 4

| | Catalyst | | | | | | | | |
|---|---|---|---|---|---|---|---|---|---|
| | A | B | C | D | E | F | G | H | I |
| | | | | | Example | | | | |
| Product Analysis, wt %[1] | 1 | 2 | 3 | 4 | 5 | 6 | 7 | 8 | 9 |
| Water | 21.06 | 21.50 | 21.61 | 21.90 | 19.02 | 18.21 | 16.54 | 17.27 | 21.72 |
| Methanol | 0 | 0.10 | 0.15 | 0.75 | 4.05 | 4.64 | 5.37 | 6.48 | 0.08 |
| Dimethylether | 0 | 0 | 0 | 0 | 0 | 0 | 0 | 0 | 0 |
| Benzene | 1.39 | 1.18 | 0 | 0 | 0 | 0 | 0 | 0 | 0.43 |
| Toluene | 43.82 | 44.77 | 50.54 | 54.86 | 70.21 | 72.00 | 75.33 | 74.11 | 49.63 |
| Ethylbenzene | 0 | 0 | 0 | 0 | 0 | 0 | 0 | 0 | 0 |
| p-Xylene (PX) | 7.11 | 6.85 | 12.35 | 14.30 | 5.58 | 4.49 | 2.65 | 2.03 | 5.86 |
| m-Xylene (MX) | 15.44 | 14.88 | 8.94 | 4.20 | 0.47 | 0.26 | 0.11 | 0.11 | 12.48 |
| o-Xylene (OX) | 6.86 | 6.58 | 3.46 | 1.82 | 0.30 | 0.17 | 0 | 0 | 5.38 |
| Ethyltoluenes | 1.01 | 0.95 | 0.42 | 0.26 | 0.14 | 0.11 | 0 | 0 | 1.18 |
| Trimethylbenzenes | 2.94 | 2.84 | 2.33 | 1.75 | 0.22 | 0.12 | 0 | 0 | 2.81 |
| C10+ | 0.36 | 0.36 | 0.20 | 0.16 | 0 | 0 | 0 | 0 | 0.41 |
| Total Aromatic Products, wt % | 35.11 | 33.64 | 27.70 | 22.49 | 6.71 | 5.15 | 2.76 | 2.14 | 28.55 |
| Total Xylenes, wt % | 29.41 | 28.31 | 24.75 | 20.32 | 6.35 | 4.92 | 2.76 | 2.14 | 23.72 |
| Total Xylenes Selectivity, wt % | 83.77 | 84.16 | 89.35 | 90.35 | 94.63 | 95.53 | 100 | 100 | 83.08 |
| p-Xylene Selectivity, wt % | 24.17 | 24.20 | 49.90 | 70.37 | 87.87 | 91.26 | 96.01 | 94.86 | 24.70 |

[1]Liquid product stream analysis

TABLE 5

| | Catalyst | | | | | |
|---|---|---|---|---|---|---|
| | J | K | L | M | N | O |
| | | | Example | | | |
| Product Analysis, wt %[1] | 10 | 11 | 12 | 13 | 14 | 15 |
| Water | 16.33 | 16.80 | 19.73 | 16.38 | 15.79 | 16.12 |
| Methanol | 0.54 | 0.50 | 2.39 | 1.72 | 2.13 | 0.45 |
| Dimethylether | 0 | 0 | 0 | 0 | 0 | 0 |
| Benzene | 0 | 0 | 0 | 0 | 0 | 0.39 |
| Toluene | 57.02 | 57.76 | 60.57 | 64.47 | 66.10 | 52.37 |
| Ethylbenzene | 0 | 0 | 0 | 0 | 0 | 0 |
| p-Xylene (PX) | 19.55 | 20.18 | 15.05 | 15.24 | 13.37 | 8.54 |
| m-Xylene (MX) | 3.12 | 2.04 | 0.76 | 0.84 | 0.96 | 13.70 |
| o-Xylene (OX) | 1.56 | 1.07 | 0.48 | 0.53 | 0.68 | 5.50 |
| Ethyltoluenes | 0.35 | 0.36 | 0.32 | 0.35 | 0.33 | 0.67 |
| Trimethylbenzenes | 1.39 | 1.17 | 0.45 | 0.47 | 0.55 | 2.05 |
| C10+ | 0.12 | 0.11 | 0.25 | 0 | 0.09 | 0.20 |
| Total Aromatic Products, wt % | 26.09 | 24.93 | 17.31 | 17.43 | 15.98 | 31.05 |
| Total Xylenes, wt % | 24.23 | 23.29 | 16.29 | 16.61 | 15.01 | 27.74 |
| Total Xylenes Selectivity, wt % | 92.87 | 93.42 | 94.11 | 95.30 | 93.93 | 89.34 |
| p-Xylene Selectivity, wt % | 80.69 | 86.65 | 92.39 | 91.75 | 89.07 | 30.79 |

[1]Liquid product stream analysis

TABLE 6

| | Catalyst | | | |
|---|---|---|---|---|
| | P | Q | R | S |
| | | Example | | |
| Product Analysis, wt %[1] | 16 | 17 | 18 | 19 |
| Water | 17.65 | 16.46 | 16.22 | 16.58 |
| Methanol | 0.57 | 0.85 | 0.98 | 2.27 |
| Dimethylether | 0 | 0 | 0 | 0 |
| Benzene | 0 | 0 | 0 | 0 |
| Toluene | 56.17 | 60.21 | 61.74 | 66.50 |
| Ethylbenzene | 0 | 0 | 0 | 0 |
| p-Xylene (PX) | 19.87 | 18.17 | 18.34 | 13.34 |
| m-Xylene (MX) | 2.53 | 1.76 | 1.05 | 1.06 |

TABLE 6-continued

| | Catalyst | | | |
|---|---|---|---|---|
| | P | Q | R | S |
| | Example | | | |
| Product Analysis, wt %[1] | 16 | 17 | 18 | 19 |
| o-Xylene (OX) | 1.47 | 0.98 | 0.58 | 0.25 |
| Ethyltoluenes | 0.35 | 0.36 | 0.41 | 0 |
| Trimethylbenzenes | 1.25 | 1.08 | 0.68 | 0 |
| C10+ | 0.13 | 0.12 | 0 | 0 |
| Total Aromatic Products, wt % | 25.60 | 22.47 | 21.06 | 14.65 |
| Total Xylenes, wt % | 23.87 | 20.91 | 19.97 | 14.65 |
| Total Xylenes Selectivity, wt % | 93.24 | 93.06 | 94.82 | 100 |
| p-Xylene Selectivity, wt % | 83.24 | 86.90 | 91.84 | 91.06 |

[1]Liquid product stream analysis

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

We claim:

1. A method of preparing a xylene product comprising:
   forming a slurry of a binder-free ZSM-5 zeolite having a $SiO_2/Al_2O_3$ mole ratio of from about 250 to about 3000 and an aqueous solution of a phosphorus compound;
   removing water from the slurry to provide a non-steamed, phosphorus treated ZSM-5 zeolite catalyst without deposition of phosphorus onto the catalyst by organophosphorus vapor deposition, and wherein the resulting non-steamed, phosphorus treated ZSM-5 zeolite catalyst has a pore volume of from 0.2 ml/g or less; and
   contacting the treated zeolite catalyst with an aromatic feed of toluene and methanol under reaction conditions suitable for toluene methylation to provide a xylene product having greater than 80% para-xylene by total mixed xylenes.

2. The method of claim 1, wherein:
   the zeolite catalyst has a pore volume of less than 0.18 ml/g.

3. The method of claim 1, wherein:
   the phosphorus compound includes at least one of phosphoric acid ($H_3PO_4$), phosphorus acid ($H_3PO_3$) and ammonium hydrogen phosphate (($NH_4$)$_2$HPO$_4$).

4. The method of claim 1, wherein:
   the phosphorus content of the treated ZSM-5 zeolite catalyst is from 0.04 g P/g zeolite or more.

5. The method of claim 1, wherein;
   contacting the treated zeolite catalyst with an aromatic feed of toluene and methanol under reaction conditions suitable for toluene methylation provides greater than 90% total xylene selectivity and greater than 85% para-xylene selectivity of the xylene product.

6. The method of claim 1, wherein:
   the phosphorus content of the treated ZSM-5 zeolite catalyst is greater than 0.09 g P/g zeolite.

7. The method of claim 1, wherein:
   the phosphorus compound is a phosphorus-containing acid.

8. The method of claim 1, wherein:
   the zeolite catalyst has a ratio of framework aluminum to extra-framework aluminum as measured by $^{27}$Al MAS-NMR of 0.12 to 0.25.

9. The method of claim 1, wherein:
   the zeolite catalyst had a $SiO_2/Al_2O_3$ mole ratio of from about 300 to about 3000 prior to phosphorus treatment.

10. The method of claim 1, wherein:
    the pore volume is reduced from about 30% to less than about 60% from that of the untreated zeolite.

11. A method of preparing a xylene product comprising:
    forming a slurry of a binder-free ZSM-5 zeolite having a $SiO_2/Al_2O_3$ mole ratio of from about 250 to about 3000 and an aqueous solution of a phosphorus compound;
    removing water from the slurry to provide a non-steamed, phosphorus treated ZSM-5 zeolite catalyst without deposition of phosphorus onto the catalyst by organophosphorus vapor deposition, and wherein the resulting non-steamed, phosphorus treated ZSM-5 zeolite catalyst has a phosphorus content of from 0.04 g P/g zeolite or more and a pore volume of from 0.2 ml/g or less; and
    contacting the treated zeolite catalyst with an aromatic feed of toluene and methanol under reaction conditions suitable for toluene methylation to provide a xylene product having greater than 80% para-xylene by total mixed xylenes.

12. The method of claim 11, wherein:
    the phosphorus content is from 0.09 g P/g zeolite to 0.15 g P/g zeolite.

13. The method of claim 11, wherein:
    the phosphorus compound is a phosphorus-containing acid.

14. The method of claim 11, wherein:
    the zeolite catalyst has a pore volume of less than 0.18 ml/g.

15. The method of claim 11, wherein:
    the zeolite catalyst has a $SiO_2/Al_2O_3$ mole ratio of from about 250 to 1000 prior to phosphorus treatment.

16. The method of claim 11, wherein:
    the zeolite catalyst provides greater than 90% para-xylene selectivity of mixed xylenes when used in toluene methylation.

17. The method of claim 11, wherein:
    the zeolite catalyst had a $SiO_2/Al_2O_3$ mole ratio of from about 300 to about 3000 prior to phosphorus treatment.

18. The method of claim 11, wherein:
    the zeolite catalyst has a ratio of framework aluminum to extra-framework aluminum as measured by $^{27}$Al MAS-NMR of 0.12 to 0.25.

19. The method of claim 11, wherein:
    the pore volume is reduced from about 30% to less than about 60% from that of the untreated zeolite.

* * * * *